United States Patent [19]

Danner et al.

[11] 4,389,259

[45] Jun. 21, 1983

[54] ASYMMETRICAL DIESTERS OF ORTHOPHOSPHORIC ACID USEFUL AS CORROSION INHIBITORS

[75] Inventors: Bernard Danner, Riedisheim, France; Hartmut Mau, Istein, Fed. Rep. of Germany; Hans Stettler, Basel, Switzerland

[73] Assignee: Sandoz Ltd., Basel, Switzerland

[21] Appl. No.: 257,379

[22] Filed: Apr. 24, 1981

[30] Foreign Application Priority Data

Apr. 30, 1980 [CH] Switzerland ............... 3345/80
Jun. 20, 1980 [CH] Switzerland ............... 4756/80
Jan. 9, 1981 [CH] Switzerland ............... 126/81

[51] Int. Cl.$^3$ ................ B05D 7/14; C23F 11/16
[52] U.S. Cl. ................ 148/6.15 R; 106/14.12; 148/6.15 Z; 148/6.17; 252/389 A; 260/429.9; 260/963
[58] Field of Search ............ 148/6.15 R, 6.15 Z, 148/6.17; 106/14.12; 260/429.9, 963; 252/389 A

[56] References Cited

U.S. PATENT DOCUMENTS 2,742,369 4/1956 Hatch .
2,941,953 6/1960 Hatch .
3,380,927 4/1968 Edelstein et al. .
3,510,436 5/1970 Silverstein et al. .

3,846,071 11/1974 Redmore .

FOREIGN PATENT DOCUMENTS 1012418 12/1965 United Kingdom .

*Primary Examiner*—James R. Hoffman
*Attorney, Agent, or Firm*—Gerald D. Sharkin; Richard E. Vila; Thomas C. Doyle

[57] ABSTRACT

Asymmetrical phosphate esters of formula I

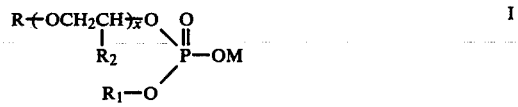

in which
R is $C_{1-20}$alkyl,
$R_1$ is $C_{1-20}$alkyl,
$R_2$ is hydrogen or methyl
x is 1–15 and
M is hydrogen, an alkali metal ion or an equivalent of an alkali earth metal or zinc ion are effective inhibitors of oxidative corrosion of metals in the presence of electrolytes. They may be used alone or in conjunction with further additives, and are preferably dissolved in the electrolyte with which the metal is to come in contact.

15 Claims, No Drawings

ASYMMETRICAL DIESTERS OF ORTHOPHOSPHORIC ACID USEFUL AS CORROSION INHIBITORS

This invention relates to the use of asymmetrical diesters of orthophosphoric acid as corrosion inhibitors, in particular as inhibitors of oxidative corrosion of metals which are in contact with weakly acidic to weakly basic electrolytes.

The invention provides a process for the inhibition of oxidative corrosion of metals in the presence of weakly acidic to weakly basic electrolytes comprising the step of contacting the metal with a compound of formula I:

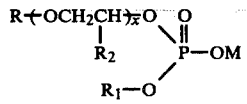

in which
R is $C_{1-20}$alkyl,
$R_1$ is $C_{1-20}$alkyl,
$R_2$ is hydrogen or methyl
x is 1–15 and
M is hydrogen, an alkali metal ion or an equivalent of an alkaline earth metal or zinc ion.

R is preferably R' where R' is $C_{8-18}$alkyl, more preferably R'' where R'' is $C_{12-16}$alkyl. $R_1$ is preferably $R_1'$ where $R_1'$ is $C_{1-5}$alkyl, more preferably $R_1''$ where $R_1''$ is $C_{2-4}$alkyl, particularly $R_1'''$, where $R_1'''$ is propyl or butyl. Preferably R and $R_1$ are straight chain alkyl groups. $R_2$ is preferably hydrogen. The value of x, which may be an average value, is preferably x' where x' is 3–12, more preferably x'' where x'' is 6–9. M is preferably M' where M' is Na, K, ½ Ca or ½Zn, more preferably M'' where M'' is Na, K or ½Zn.

Preferred compounds of formula I for use in the process of the invention are those of formula I'

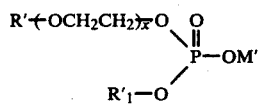

in which R', $R_1'$, x' and M' are as defined above. More preferred are compounds of formula I''

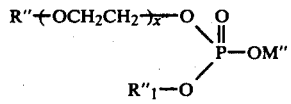

in which R'', $R_1''$, x'' and M'' are as defined above, particularly those in which $R_1''$ has the significance of $R_1'''$.

The term 'electrolyte' is intended to cover all liquids which either are aqueous systems or which contain or liberate smaller quantities of water. Examples of electrolytes are water itself, mixtures of water with organic compounds (for example water/glycol mixtures) or mineral oil products contaminated with water. By weakly acidic to weakly basic is meant a pH in the range of 3–10, preferably 5–9, more preferably 6–8.5.

Metals particularly suitable for protection against oxidative corrosion by the process of the invention are copper, iron, zinc and aluminium, or alloys containing one or more of these.

The corrosion-inhibiting compound is preferably dissolved in the electrolyte with which the metal will come in contact, the concentration of the compound of formula I in the electrolyte being preferably at least 10 ppm. Alternatively, however, the compound may be added to the electrolyte in a form which slowly releases the compound into solution, or the metal surface may be treated directly with the compound for example by painting with a paint composition containing a compound of formula I, or by dipping into or spraying with an aqueous or water/oil suspension of the compound. The latter procedure is useful for giving temporary corrosion protection to bare metal parts.

The process of the invention is preferably carried out in the presence of zinc ions. The compound of formula I may be used in the form of its zinc salt, or an inorganic zinc salt may be added to a different form of the compound. Preferably the compound of formula I is used in the form of the sodium or potassium salt in the presence of zinc nitrate.

In the preferred process in which the compound of formula I is dissolved in the electrolyte, the concentration of the compound of formula I in the electrolyte is more preferably at least 30 ppm. The upper concentration limit is not critical, but an upper limit of 1000 ppm is as a rule sufficient for all applications. The optimal concentration is in the range 50–200 ppm, preferably 60–150 ppm, particularly about 100 ppm. If the electrolyte contains corrosive substances, the content of compound of formula I should be correspondingly higher.

When the compound of formula I is used other than as its zinc salt in the presence of additional inorganic zinc salt, the weight ratio of compound of formula I to zinc ion is preferably from $10^4$:5 to $10^4$:1, more preferably from $10^4$:4 to $10^4$:1. Optional effects are obtained with a ratio of $10^4$:2. The concentration of zinc ion in the electrolyte is thus at least 0.001 ppm by weight, preferably at least 0.003 ppm. The upper limit is not critical, but a concentration of 5 ppm is normally sufficient. The preferred concentration range is 0.001–0.5 ppm, more preferably 0.01–0.1 ppm particularly 0.02–0.03 ppm.

The process according to the invention is preferably carried out by contacting the metal with a mixture of at least two components (a) and (b), of which (a) is one or more compounds of formula I, optionally together with additional zinc salts as described above, and (b) is one or more compounds selected from mercaptobenzothiazoles, benzotriazoles and sodium boroheptonate. More preferably, the metal is contacted with a mixture of at least three components (a), (b) and (c), of which (a) and (b) are as defined above and (c) is one or more compounds selected from pH-adjusting agents, biocides, anti-scaling agents, mild oxidizing agents and surfactants.

Preferably components (b) and (c) as well as (a) are soluble in the electrolyte and are added to the electrolyte together with (a). The total concentration of (a)+(b)+(c) in the electrolyte is at least 10 ppm by weight.

Preferred mercaptobenzothiazoles as component (b) are unsubstituted mercaptobenzothiazole and its alkali metal salts. Preferred components (b) are however unsubstituted benzotriazole, tolyltriazole and sodium boroheptonate, more preferably benzotriazole and sodium boroheptonate.

As possible constituents of component (c), suitable pH-adjusting agents include common inorganic and organic bases for example sodium hydroxide, sodium carbonate, sodium bicarbonate, sodium acetate, mono- or di-sodium orthophosphate, mono-, di- or tri-ethanolamine, preferably monoethanolamine.

Any known biocide which is stable under the given conditions may be used. Examples include formaldehyde, p-chlorophenylpropanediol, dilauryldimethylammonium chloride, the sodium salt of o-phenylphenol, 5,5'-dichloro-2,2'dihydroxydiphenylmethane, p-chloro-m-xylenol, octachlorocyclohexane, quaternary ammonium compounds and 2,2'-dichloro-5,5'-dihydroxydiphenyl. Such compounds are described for example in TAPPI, December 1969 Vol. 52 No. 12. The preferred biocide is 5,5'-dichloro-2,2'-dihydroxydiphenylmethane.

Examples of anti-scaling agents are hydroxycarboxylates (e.g. gluconates, heptonates), aminocarboxylates (e.g. the sodium salts of nitrilotriacetic acid, ethylenediamine tetraacetic acid or diethylenetriamine pentaacetic acid) and citric acid. Such agents are described for example in "Textile Chemist & Colorist" 1978 Vol. 10 No. 8. Preferred compounds of this type are gluconic acid, mannonic acid and related compounds, and sodium heptonate.

Suitable mild oxidizing agents include nitrate ions. These may be supplied by adding the zinc salt in (a) in the form of zinc nitrate, which is why zinc nitrate is the preferred zinc salt. When zinc nitrate is used together with the compound of formula I, the $Zn^{++}$ ions may be regarded as part of component (a) and the $NO_3^-$ ions as all or part of component (c).

Preferred surfactants are conventional non-ionic surfactants.

The concentration of component (b) in the electrolyte is preferably at least 50 ppm by weight, more preferably 50–1000 ppm, still more preferably 50–200 ppm and particularly about 100 ppm. The concentration of pH regulating agent, if present, will depend upon the initial pH of the electrolyte but will typically be from 20–1000 ppm, preferably 30–300 ppm. The concentration of biocide is preferably 0–800 ppm, more preferably 50–150 ppm. The concentration of anti-scaling agent is preferably 0–1000 ppm, more preferably 30–600 ppm. The concentration of surfactant is typically from 0 to 25% of that of the total of components (a)+(b)+(c). In general the total concentration of components (a)+(b)+(c) is preferably in the range 500–2000 ppm.

The invention further provides a corrosion-inhibiting composition comprising a compound of formula I in association with a carrier.

Preferably the composition also contains component (b) as defined above, more preferably components (b) and (c). The carrier may be a solvent, e.g. water, an alcohol, a glycol or a mixture thereof in which components (a) and optionally (b) and (c) are dissolved. This may be in the form of a concentrated solution suitable for addition to an electrolyte. The carrier may also be an aqueous or oil-water system in which the components are suspended, or may be a paint vehicle. The preparation of such compositions, which preferably contain from 1–60% by weight of compound of formula I, is conventional.

Compounds of formula I may be obtained in substantially pure form by sequential reaction of 1 mole of phosphorus oxychloride with 1 mole each of the compounds II and III $$R+OCH_2CHR_2)_xOH \qquad \text{II}$$

$$R_1-OH \qquad \text{III}$$

in any desired order, the initial product being hydrolysed and, where appropriate, transformed simultaneously into the desired salt form.

The reaction conditions are known from analogous reactions of $POCl_3$ with alcohols. Preferably the first stage of the reaction is carried out in the presence of an excess of $POCl_3$ which is then removed, for example by distillation, before the product of the first stage is further reacted with the other alcohol II or III.

The hydrolysis may be carried out in known manner by adding water to the product of the second reaction stage. If it is desired to make a compound of formula I in which M is other than hydrogen, the water used for hydrolysis should contain the corresponding cation and the pH of the reaction mixture adjusted to be neutral or weakly basic. Alternatively the free acid form of the compound of formula I may subsequently be reacted with base to give the salt forms.

An alternative procedure for the preparation of compounds of formula I is to react phosphorus oxychloride or phosphorus pentoxide with a mixture of compounds II and III at temperatures of up to 95° C., preferably up to 60° C. The product of this process is a mixture containing the compounds of formula I, which may however be used as such without further purification.

The corrosion inhibiting compositions of the invention may be added for example to aqueous systems such as domestic heating systems or aqueous or water/glycol systems such as coolants for internal combustion engines. They may also be added to the contents of fire extinguishers of the liquid or foam type, whereby after a fire has been extinguished further damage by corrosion is inhibited. Addition of a composition according to the invention to wood pulp in a paper-making machine will help to prevent corrosion of the machine parts.

The following Examples, in which all parts are percentages are by weight and all temperatures are in degrees Centigrade, illustrate the invention.

EXAMPLE 1

460.5 Parts (3 moles) phosphorus oxychloride are cooled to −10° under nitrogen, and 508 parts (1 mole) of the addition product of 7 moles ethylene oxide to 1 mole tridecyl alcohol is added dropwise with stirring over 10 hours, keeping the temperature below 30° at all times. When 36.5 parts HCl has been evolved, the excess phosphorus oxychloride is removed by distillation under reduced pressure, leaving an oily product of formula $$C_{13}H_{27}-(OCH_2CH_2)_7O-POCl_2$$

This product is then treated at 25°–30° with a solution of 74 parts (1 mole) of n-butanol in carbon tetrachloride as solvent. After a further 36.5 parts HCl have been evolved, the solvent is removed by distillation under reduced pressure, giving an oily product of formula

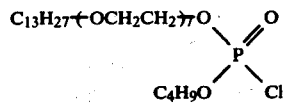

This product is then hydrolysed at room temperature with 133 parts of 30% aqueous sodium hydroxide, to give an 84% aqueous solution of the compound of formula

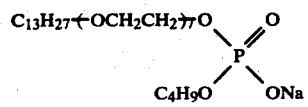

EXAMPLE 2

1040 Parts n-butanol and 265 parts of the addition product of 7 moles ethylene oxide to 1 mole tridecanol are mixed together and added dropwise to 550 parts $P_2O_5$, keeping the temperature below 60°. The product is neutralised by addition of 1430 parts 30% aqueous sodium hydroxide.

EXAMPLES 3–13

By following the procedure of Example 1 or Example 2, with suitable choice of starting materials, asymmetric phosphate esters having the general formula

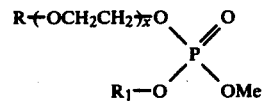

are obtained, where R, $R_1$, x and Me are as shown in Table I below

TABLE I

| Example No. | R | $R_1$ | x | Me |
|---|---|---|---|---|
| 3 | $C_2H_5$ | $C_2H_5$ | 1 | Na |
| 4 | $C_2H_5$ | $C_2H_5$ | 15 | " |
| 5 | $C_4H_9$ | $C_4H_9$ | 1 | " |
| 6 | $C_4H_9$ | $C_4H_9$ | 15 | " |
| 7 | $C_4H_9$ | $C_4H_9$ | 12 | " |
| 8 | $C_{13}H_{27}$ | $C_3H_7$ | 9 | K |
| 9 | $C_{13}H_{27}$ | $C_3H_7$ | 9 | Zn |
| 10 | $C_{15}H_{31}$ | $C_4H_9$ | 7 | Na |
| 11 | $C_{20}H_{41}$ | $C_4H_9$ | 1 | " |
| 12 | $C_{20}H_{41}$ | $C_2H_5$ | 12 | " |
| 13 | $C_{20}H_{41}$ | $C_4H_9$ | 15 | " |

EXAMPLE 14

A mixture of 67 parts of the 84% solution obtained in Example 1 and 585 parts water is stirred at room temperature and 80 parts dichlorodihydroxydiphenol are added. The mixture is stirred vigorously until a clear solution results. 90 Parts sodium boroheptonate are added, to give a clear solution. To this mixture is added portionwise 100 parts benzotriazole; the solution becomes cloudy and a precipitate is observed. Addition of 65 parts monoethanolamine causes a slight warming of the mixture, and under vigorous stirring the precipitate redissolves and a clear solution is again obtained. Finally 5 parts of a 1% aqueous zinc nitrate solution is added. The final product has a pH of 9–10.

EXAMPLES 15–35

Compositions analogous to that of Example 14 may be made in the same way using the product of Example 1 together with additional ingredients as shown in Tables 2 and 3 below:

TABLE 2

| | (percentages by weight) | | | | | | | | | | | |
|---|---|---|---|---|---|---|---|---|---|---|---|---|
| Example No. | 15 | 16 | 17 | 18 | 19 | 20 | 21 | 22 | 23 | 24 | 25 | 26 |
| Compound of Ex. 1 | 10 | 10.5 | 11.8 | 11.5 | 12 | 12 | 30 | 80 | 50 | 20 | 10 | 15 |
| Mercaptobenzothiazole | 12.5 | 12.5 | 10.0 | 10.0 | 12.5 | 10 | 20 | 5 | 10 | 5 | 20 | 10 |
| Zn(NO$_3$)$_2$ | 0.006 | 0.006 | 0.006 | 0.006 | 0.006 | 0.006 | 0.06 | 0.6 | 0.006 | 0.006 | 0.006 | 0.03 |
| Monoethanolamine | 8.0 | 8.0 | 6.5 | 6.5 | 8.0 | 6.5 | 10 | 5 | 8 | 5 | 10 | 6.5 |
| 2,2-Dichloro-5,5-dihydroxydiphenylmethane | 8.0 | 10.0 | 8.0 | 8.0 | — | — | 4 | 5 | — | — | 20 | 3.2 |
| Na—Heptonate | 5.0 | — | 9.0 | 6.0 | 9.0 | 10.0 | 30 | 5 | 20 | 60 | 40 | — |
| Water | 36.5 | 36.6 | 31.1 | 35.0 | 35.5 | 36.5 | 6 | — | 12 | 10 | — | 62.6 |
| Na Gluconate | — | — | — | — | — | — | — | — | — | — | — | 2.7 |

TABLE 3

| | (percentage by weight) | | | | | | | | |
|---|---|---|---|---|---|---|---|---|---|
| Example No. | 27 | 28 | 29 | 30 | 31 | 32 | 33 | 34 | 35 |
| Compound of Example 1 | 4.0 | 40.0 | 40.0 | 50.0 | 40.0 | 35.0 | 45.0 | 4.0 | 40.0 |
| Benzotriazole | 10.0 | 10.0 | 10.0 | 20.0 | 10.0 | 15.0 | 10.0 | 20.0 | 20.0 |
| Na—Boroheptonate | 22.0 | 25.0 | 22.0 | 20.0 | 20.0 | 22.0 | 30.0 | 30.0 | 20.0 |
| Zn(NO$_3$)$_2$ | 0.06 | 0.006 | 0.03 | 0.006 | 0.03 | 0.006 | 0.06 | 0.06 | 0.03 |
| Monoethanolamine | 6.5 | 5.0 | 6.5 | 10.0 | 6.5 | 9.0 | 6.5 | 10.0 | 10.0 |
| 2,2-Dichloro-5,5-dihydroxydiphenol | 8.0 | 8.0 | 8.0 | — | 8.0 | 8.0 | — | — | — |
| Water | 39.5 | 12.0 | 13.5 | — | 10.0 | 8.0 | — | 26.0 | — |
| Nonionic Surfactant | 10.0 | — | — | — | 5.0 | 3.0 | 8.5 | 10.0 | 10.0 |

EXAMPLE 36

The composition of Example 18 was tested for corrosion inhibition according to DIN 50 905 pages 1–2, using a fully immersed metal sample in an aerated solution stirred at 250 rpm. The electrolytes used were:
(a) tap water of 18° hardness
(b) brine containing 3% NaCl
(c) an ethylene glycol/water mixture (55:45).

Test samples were of (i) building steel U St 37-1 (ii) copper alloy No. 20060 (DIN 17007) (iii) cast zinc and (iv) pure (99.9%) aluminium.

A concentration of 0.5 g/l of the composition of Example 18 in electrolytes (a) and (c) was sufficient to greatly reduce corrosion of all four metal samples. For electrolyte (b) a concentration of 1.0 g/l was required.

Similar results are obtained for the compositions of Examples 14–17 and 19–35.

What is claimed is:

1. A process for the inhibition of oxidative corrosion of metals in the presence of weakly acidic to weakly basic electrolytes comprising the step of contacting the metal with an effective amount of a compound of formula I:

$$R-(OCH_2CH)_x-O\diagdown_{P-OM}^{O}$$
$$R_2 \quad \quad \quad \parallel$$
$$R_1-O\diagup$$

in which
R is $C_{8-18}$alkyl,
$R_1$ is $C_{2-4}$alkyl,
$R_2$ is hydrogen or methyl,
x is 1–15, and
M is hydrogen, an alkali metal ion or an equivalent of an alkaline earth metal or zinc ion.

2. A process according to claim 1 in which the compound of formula I is dissolved in the electrolyte.

3. A process according to claim 1 in which the compound of formula I is contacted with the metal in the presence of zinc ions.

4. A process according to claim 3 in which the concentration of zinc ion is 0.001–0.5 ppm.

5. A process according to claim 1 in which the metal is contacted with a mixture of at least two components (a) and (b), of which (a) is one or more compounds of formula I, and (b) is one or more compounds selected from mercaptobenzothiazoles, benzotriazoles and sodium boroheptonate.

6. A process according to claim 5 in which the metal is contacted with a mixture of at least three components (a), (b) and (c), of which (a) and (b) are as defined in claim 4 and (c) is one or more compounds selected from pH-adjusting agents, biocides, anti-scaling agents, mild oxidizing agents and surfactants.

7. A process according to claim 6 in which the biocide is 5,5′dichloro-2,2′-dihydroxydiphenylmethane.

8. A process according to claim 6 in which the antiscaling agent is gluconic acid, mannonic acid or sodium heptonate.

9. A process according to claim 6 in which the mild oxidizing agent is nitrate ion.

10. A process according to claim 6 in which the components (a) (b) and (c) are all dissolved in the electrolyte, the total concentration of (a)+(b)+(c) in the electrolyte being at least 10 ppm by weight.

11. A process according to claim 10 in which the concentration of component (a) is 30–1000 ppm.

12. A process according to claim 10 in which the concentration of component (b) is 50–1000 ppm.

13. A process according to claim 10 in which the total concentration of components (a)+(b)+(c) is 500–2000 ppm.

14. A process as claimed in claim 1 in which the metal is contacted with a compound of formula I':

$$R'-(OCH_2CH_2)_{x'}-O\diagdown_{P-OM'}^{O}$$
$$R'_1-O\diagup$$

in which
R' is $C_{8-18}$alkyl
$R_1'$ is $C_{2-4}$alkyl
x' is 3–12 and
M' is Na, K, ½Ca or ½Zn.

15. A process as claimed in claim 1 in which the metal is contacted with a compound of formula I":

$$R''-(OCH_2CH_2)_{x''}-O\diagdown_{P-OM''}^{O}$$
$$R''_1-O\diagup$$

in which
R" is $C_{12-16}$alkyl
$R_1''$ is $C_{2-4}$alkyl
x" is 6–9 and
M" is Na, K or ½Zn.

* * * * *